(12) United States Patent
Wagoner

(10) Patent No.: US 11,980,305 B1
(45) Date of Patent: May 14, 2024

(54) DAMPED ARTICULATION SYSTEM

(71) Applicant: Jeffery James Wagoner, Indiantown, FL (US)

(72) Inventor: Jeffery James Wagoner, Indiantown, FL (US)

( * ) Notice: Subject to any disclaimer, the term of this patent is extended or adjusted under 35 U.S.C. 154(b) by 662 days.

(21) Appl. No.: 17/157,153

(22) Filed: Jan. 25, 2021

Related U.S. Application Data

(60) Provisional application No. 63/064,019, filed on Aug. 11, 2020.

(51) Int. Cl.
| | | |
|---|---|---|
| *B25J 9/14* | (2006.01) | |
| *A47G 21/08* | (2006.01) | |
| *A61F 4/00* | (2006.01) | |
| *F16F 7/104* | (2006.01) | |
| *F16F 15/129* | (2006.01) | |

(52) U.S. Cl.
CPC ............... *A47G 21/08* (2013.01); *A61F 4/00* (2013.01); *F16F 7/104* (2013.01); *F16F 15/129* (2013.01); *A47G 2200/046* (2013.01)

(58) Field of Classification Search
CPC ... B25J 11/00; B25J 18/04; B25J 19/00; B25J 9/04; B25J 9/10; B25J 9/12; B25J 9/14; B25J 9/16; A47G 21/08; A47G 2200/046; A61F 4/00; F16F 7/104; F16F 15/129
USPC .................... 188/290, 293, 294, 381; 623/65
See application file for complete search history.

(56) References Cited

U.S. PATENT DOCUMENTS

| | | | |
|---|---|---|---|
| 4,938,322 A * | 7/1990 | Sugasawara | ............ F16F 9/103 188/290 |
| 5,282,711 A | 2/1994 | Frische | |
| 5,400,878 A * | 3/1995 | D'Anna | .................... F16F 9/52 188/293 |
| 5,630,276 A | 5/1997 | Weinstein | |
| 6,695,794 B2 | 2/2004 | Kaiser et al. | |
| 6,705,815 B1 | 3/2004 | Bennett et al. | |
| 8,308,664 B2 | 11/2012 | Pathak et al. | |
| 8,442,669 B2 | 5/2013 | Dekar | |
| 10,004,625 B2 | 6/2018 | Fogelberg et al. | |

(Continued)

FOREIGN PATENT DOCUMENTS

| | | |
|---|---|---|
| BR | 202016024314 | 5/2018 |
| CN | 102990669 | 3/2013 |

(Continued)

*Primary Examiner* — Christopher P Schwartz

(57) ABSTRACT

A damped articulation system facilitates operation of a handheld implement and includes a damped pivot joint assembly comprising a pivot joint assembly including at least one pivot joint unit having a plurality of pivot joint members movably interconnected to one another. A damping assembly having a plurality of damping members interconnected to different ones of the pivot joint members and being movable therewith. The damping assembly further comprising a damping compound disposed between adjacent ones of a plurality of damping surfaces of the damping members, wherein the damping compound serves to minimize oscillation of the damped pivot joint assembly during movement of the pivot joint members having one or more damping members interconnected thereto relative to one another. A handheld implement assembly including a handle having a handheld implement attached thereto is interconnected to a terminal portion of the damped pivot joint assembly.

19 Claims, 12 Drawing Sheets

(56) References Cited

U.S. PATENT DOCUMENTS

| | | |
|---|---|---|
| 10,165,881 B2 | 1/2019 | Marciano |
| 10,264,904 B1 | 4/2019 | Kim et al. |
| 10,271,770 B2 | 4/2019 | Pathak et al. |
| 10,562,180 B2 * | 2/2020 | Telleria .................... F16J 3/04 |
| 10,583,061 B2 | 3/2020 | Pathak et al. |
| 2015/0231942 A1 | 8/2015 | Trangbaek et al. |
| 2017/0326023 A1 | 11/2017 | Zhu et al. |
| 2019/0022871 A1 | 1/2019 | Liu |
| 2019/0038222 A1 | 2/2019 | Krimon et al. |
| 2020/0029710 A1 | 1/2020 | Jensen et al. |

FOREIGN PATENT DOCUMENTS

| | | |
|---|---|---|
| GB | 2553624 | 3/2018 |
| JP | 2008238338 | 10/2008 |
| KR | 20180123793 | 11/2018 |
| KR | 20200032784 | 3/2020 |
| WO | 2020047666 | 3/2020 |

\* cited by examiner

DAMPED ARTICULATION SYSTEM

CROSS-REFERENCE TO RELATED APPLICATIONS

This application claims the benefit of U.S. Provisional Patent Application Ser. No. 63/064,019 filed on Aug. 11, 2020, which is incorporated by reference herein in its entirety.

FIELD OF THE INVENTION

The present invention relates generally to a damped articulation system.

BACKGROUND OF THE INVENTION

There are a variety of ailments, diseases and age-related conditions that can result in involuntary movements or tremors in a person's arms and hands. These can vary from an occasional physical tick or slight jerking motion, to very mild tremors which may barely be visible to the untrained eye, to extreme and highly noticeable tremors and/or involuntary movements, such as in persons afflicted with Parkinson's disease, notably, celebrities such as Muhammed Ali and Michael J. Fox.

For those who suffer with these types of conditions, even simple daily activities become difficult, if not impossible. For some, they are no longer able to manipulate a knife, a fork and/or a spoon with enough control to be able to feed themselves. A simple meal often becomes a very messy operation, and in more severe cases, the person needs to be fed by a caregiver, often a family member or a friend. As one might imagine, this can create feelings of frustration and embarrassment for a person who, while fully aware and mentally competent, is no longer able to carry out even the simplest of physical tasks due solely to his or her particular ailment or affliction.

Attempts have been made to address this problem with self-contained hand held devices that use electronic components and actuators manipulating an integral utensil. Devices have been proposed which sense small unwanted or uncontrolled movements of a person's hands and/or arms, and process that information via a computer. The computer analyzes the data and transmits signals to an actuator in an attempt to create an opposite and proportional movement, such as to an attached eating utensil, in an effort to counter the original tremor-induced motion, such that the person can attempt to feed himself or herself while minimizing the amount of mess which occurs due to missing one's mouth in the process. Further, such a device does nothing to help stabilize a plate or bowl from which a person with mild tremors may be attempting to feed himself or herself.

While such a device may provide relief for individuals exhibiting only mild tremors, it is believed incapable of providing adequate compensatory movement of the utensil when it encounters larger unwanted or uncontrolled movements of a person's hands and/or arms, such as occur in persons experiencing moderate or severe tremors. Presently there is no known solution for individuals suffering with more pronounced, i.e. moderate to severe, tremors.

Accordingly, there is an established need for a solution to one or more of the foregoing problems.

SUMMARY OF THE INVENTION

The present invention is generally directed to a damped articulation system.

In a first implementation of the invention, a damped articulation system which facilitates operation of a handheld implement proximate a support surface by a user afflicted with tremors may comprise: a damped pivot joint assembly interconnected to a portion of the support surface; the damped pivot joint assembly comprising a pivot joint assembly including at least one pivot joint unit having at least two pivot joint members interconnected in a movable relation to one another; the damped pivot joint assembly further comprising a damping assembly having a plurality of damping members, at least one of the plurality of damping members interconnected to a different one of each of the at least two pivot joint members and movable therewith; each of the plurality of damping members comprising at least one damping surface, the at least one damping surface of each of the plurality of damping members disposed in a contacting orientation with at least one damping surface of a different one of the plurality of damping members; the damping assembly further comprising a damping compound disposed between adjacent ones of the plurality of damping surfaces disposed in the contacting orientation with one another, the damping compound exhibiting a dynamic viscosity sufficient to minimize oscillation of the damped pivot joint assembly during movement of the at least two pivot joint members, each having at least one of the plurality of damping members interconnected thereto, relative to one another; and a handheld implement assembly including a handle having the handheld implement attached thereto, the handle further interconnected to a portion of the damped pivot joint assembly.

In a second aspect, the damped articulation system can include a plurality of pivot members each having a fixed end and an oppositely disposed pivot end.

In another aspect, the damped articulation system may have a plurality of pivot members each comprising a pivot aperture through a pivot end thereof.

In a further aspect, the damped articulation system can include at least one pivot joint unit comprising a pivot member operatively positioned through a pivot aperture of each of a plurality of pivot members thereby movably interconnecting the plurality of pivot members to one another.

In one other aspect, the damped articulation system may have a fixed end of at least one pivot member interconnected to a portion of a support surface.

In yet another aspect, the damped articulation system can include a fixed end of at least one pivot member attached to a portion of a handheld implement assembly.

In still one further aspect, the damped articulation system may have a damping assembly comprising a plurality of damping members interconnected to different ones of each of at least two pivot joint members and are movable therewith.

In yet one other aspect, the damped articulation system can include at least some of a plurality of damping members comprising a plurality of damping surfaces, wherein the plurality of damping surfaces are disposed on opposite sides of a corresponding one of the plurality of damping members.

In still another aspect, the damped articulation system may have a plurality of damping members comprising a plurality of damping surfaces, wherein the plurality of damping surfaces are generally planar.

In yet one further aspect, the damped articulation system can include a plurality of damping members comprising a plurality of damping surfaces, wherein the plurality of damping surfaces are generally concentric.

In still one other aspect, the damped articulation system may have a plurality of damping members disposed such that the plurality of damping surfaces are disposed in an alternating contacting relation with one another.

In yet another aspect, the damped articulation system can include a plurality of damping surfaces constructed of a material having a static friction coefficient of about 0.04 to about 0.75, or of about 0.04 to about 1.25.

In still one further aspect, the damped articulation system may have at least some of a plurality of damping surfaces constructed of polished stainless steel.

In yet one other aspect, the damped articulation system can include a damping compound comprising an amount of polydimethylsiloxane.

In still another aspect, the damped articulation system may have a damping compound comprising a dynamic viscosity of at least about 2,000 centipoise.

In yet one further aspect, the damped articulation system can include a handheld implement comprising an eating utensil, a writing instrument, and/or a handheld tool.

In still one other aspect, the damped articulation system may have a handheld implement comprising a glove and/or a secondary hand support member.

In yet another aspect, the damped articulation system can include a mounting assembly dimensioned and configured to be at least temporarily secured to a portion of a support surface; a damped pivot joint assembly comprising a pivot joint assembly including a plurality of pivot joint units operatively interconnected to one another, wherein at least one of the plurality of pivot joint units is movable in an x-plane, at least one of the plurality of pivot joint units is movable in a y-plane, and at least one of the plurality of pivot joint units is movable in a z-plane; each of the plurality of pivot joint units having at least two pivot joint members interconnected in a movable relation to one another; the damped pivot joint assembly further comprising a damping assembly having a plurality of damping members, wherein each of the at least two pivot joint members of at least some of the plurality of pivot joint units comprises a plurality of different ones of the plurality of damping members interconnected thereto and movable therewith; each of the plurality of damping members comprising at least one damping surface, each damping surface of each different one of the plurality of damping members interconnected to corresponding ones of the at least two pivot joint members of each of the plurality of pivot joint units disposed in an alternating contacting orientation relative to one another; the damping assembly further comprising a damping compound disposed between adjacent ones of the plurality of damping surfaces, the damping compound exhibiting a dynamic viscosity sufficient to minimize oscillation of the damped pivot joint assembly during movement of the at least two pivot joint members, each having a plurality of damping members interconnected thereto, relative to one another; an articulating arm assembly having at least one arm member, wherein opposite ends of the at least one arm member are interconnected to different ones of the plurality of pivot joint units; a handheld implement assembly including a handle having the handheld implement attached thereto, a portion of the handheld implement assembly interconnected to a terminal one of the plurality of pivot joint units; and a proximal one of the plurality of pivot joint units interconnected to a portion of the mounting assembly.

In still one further aspect, the damped pivot joint assembly may have a pivot joint assembly comprising at least two pivot joint members interconnected in a movable relation to one another; a damping assembly having a plurality of damping members, at least one of the plurality of damping members interconnected to a different one of each of the at least two pivot joint members and movable therewith; each of the plurality of damping members comprising at least one damping surface disposed in a contacting orientation with at least one damping surface of a different one of the plurality of damping members; and the damping assembly further comprising a damping compound disposed between adjacent ones of the plurality of damping surfaces disposed in the contacting orientation with one another, the damping compound exhibiting a dynamic viscosity sufficient to minimize oscillation of the damped pivot joint assembly during movement of the at least two pivot joint members, each having at least one of the plurality of damping members interconnected thereto, relative to one another.

These and other objects, features, and advantages of the present invention will become more readily apparent from the attached drawings and the detailed description of the embodiments, which follow.

BRIEF DESCRIPTION OF THE DRAWINGS

The embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "top", "bottom", "left", "right", "front", "rear", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed to a damped articulation system.

Figure 1:
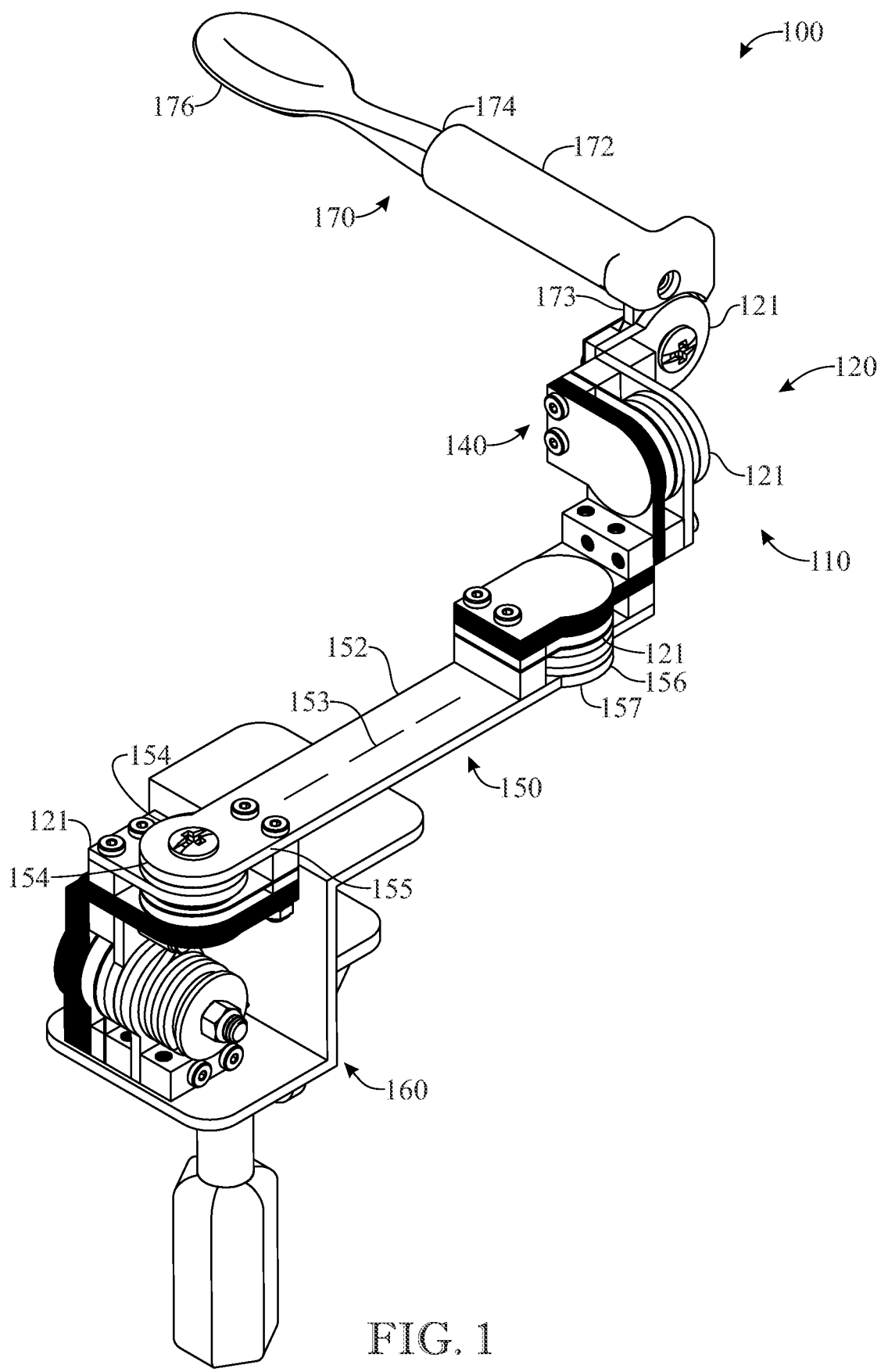
FIG. 1 presents a perspective view of one illustrative embodiment of a damped articulation system, in accordance with the present invention.

Referring initially to FIG. 1, presented therein is a perspective view of one illustrative embodiment of a damped articulation system, generally as shown as at 100, in accordance with the present invention. A damped articulation system 100 in accordance with at least one embodiment of the present invention comprises a damped pivot joint assembly 110 including a pivot joint assembly 120 having at least one pivot joint unit 121, the pivot joint unit 121 having at least two pivot joint members 122 interconnected in a movable relation to one another. In one embodiment, a damped pivot joint assembly 110 comprises a pivot joint assembly 120 having a plurality of pivot joint units 121 operatively interconnected to one another to facilitate articulation of a damped articulation system 100, such as is shown best by way of example in the illustrative embodiment of FIG. 1.

As also shown in FIG. 1, at least one embodiment of a damped pivot joint assembly 110 includes a pivot joint assembly 120 comprising a plurality of pivot joint units 121 operatively interconnected to one another, wherein at least one of the plurality of pivot joint units 121 is movable in an x-plane, at least one of the plurality of pivot joint units 121 is movable in a y-plane, and at least one of the plurality of pivot joint units 121 is movable in a z-plane. As will be appreciated, by arranging a plurality of pivot joint units 121 of pivot joint assembly 120 in each of the x-plane, the y-plane and the z-plane, the present damped articulation system 100 is operable through a full range of motion in three-dimensional space, including the normal planes of motion of a person eating from a plate with an eating utensil.

A damped pivot joint assembly 110 in accordance with the present invention further comprises a damping assembly 140, as may be seen, once again, in the illustrative embodiment of FIG. 1. In at least one embodiment, a damping assembly 140 includes a plurality of damping members 141, 144, wherein at least one of the plurality of damping members 141, 144 is interconnected to a different one of at least two pivot joint members 122 of a pivot joint unit 121. In at least one further embodiment, each of a plurality of damping members 141, 144 is movable with a different one of each of at least two pivot joint members 122 of a pivot joint unit 121. Additionally, each of the plurality of damping members 141, 144 comprises at least one damping surface 142, 145, wherein at least one damping surface 142, 145 of each of the plurality of damping members 141, 144 is disposed in an operative contacting orientation with at least one damping surface 142, 145 of a different one of the plurality of damping members 141, 144, as is discussed in greater detail hereinafter.

A damped articulation system 100 in accordance with at least one embodiment of the present invention further comprises an articulating arm assembly 150. Looking again to FIG. 1, an articulating arm assembly 150 includes at least one arm member 152 interconnected between oppositely disposed pivot joint units 121. In at least one embodiment, an arm member 152 comprises a first end 154 having a first interconnect portion 155 interconnected to one of a plurality of pivot joint units 121, and an oppositely disposed second end 156 having a second interconnect portion 157 interconnected to a different one of a plurality of pivot joint units 121, such as may be seen best in FIG. 1. As further shown in FIG. 1, an arm member 152 of an articulating arm assembly 150 in accordance with at least one embodiment comprises an arm axis 153, wherein arm member 152 is articulated between oppositely disposed pivot joint units 121 about arm axis 153. It is to be appreciated that an articulating arm assembly 150 of a damped articulation system 100 may comprise a plurality of arm members 152 each interconnected to at least one pivot joint unit 121 of a pivot joint assembly 120, in accordance with the present invention.

A damped articulation system 100 in at least one embodiment further comprises a mounting assembly 160 dimensioned and configured to at least temporarily secure the damped articulation system 100 to a portion of a support surface SS, as is also discussed in greater detail hereinafter.

With reference once again to FIG. 1, a damped articulation system 100 in accordance with at least one embodiment of the present invention further comprises a handheld implement assembly 170. A handheld implement assembly 170 in at least one embodiment includes an implement handle 172 having a handle interconnect 173 at one end to attach the implement handle 172 to at least a portion of a terminal pivot joint unit 121. In one further embodiment, an implement handle 172 has an implement interconnect 174 disposed on an opposite end thereof to facilitate attachment of a handheld implement 176 thereto in an operable orientation. A handheld implement 176 in accordance with the present invention may include but is in no manner limited to an eating utensil such as a knife, a fork, or a spoon. As such, an implement interconnect 174 in accordance with at least one embodiment of the present invention comprises a quick-connect type fitting to facilitate removal of an eating utensil for cleaning. A handheld implement 176 in accordance with the present invention may also include, but again is in no manner limited to, a writing instrument such as a pen, a pencil, a marker, a paintbrush, or a handheld tool, such as, by way of example, a screwdriver, a wrench, a pair of pliers, an awl, etc., just to name a few. It is to be appreciated that a handheld implement 176 in accordance with the present invention may comprise a hand stabilizing implement such as, by way of example, a glove and/or a secondary hand support member.

Figure 2A:
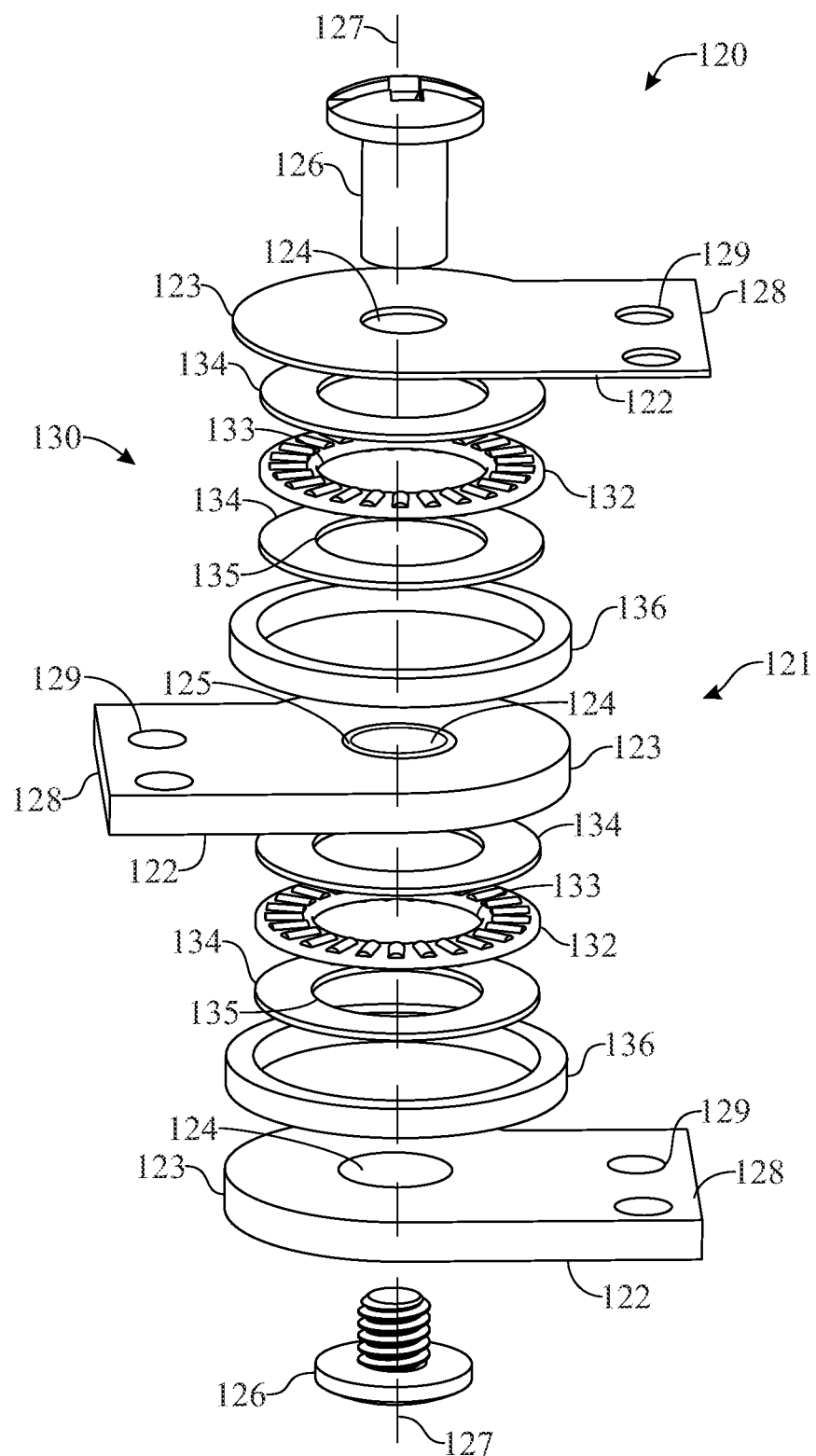
FIG. 2A presents an exploded perspective view of the pivot joint unit of the pivot joint assembly of FIG. 2, in accordance with the present invention.
Figure 2:
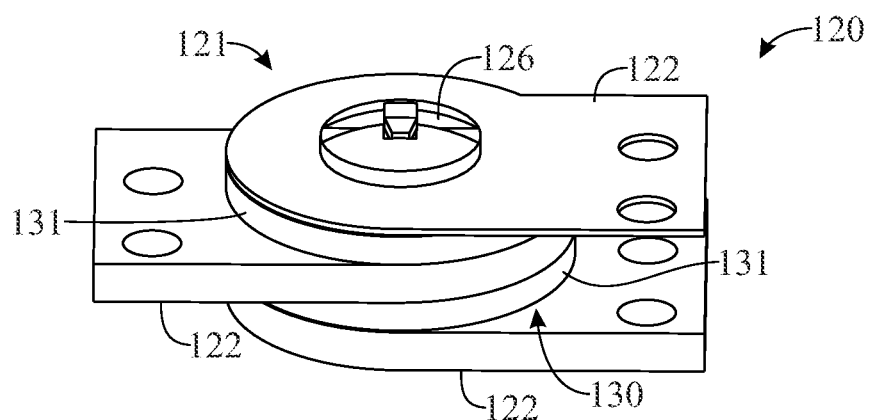
FIG. 2 presents a perspective view of one illustrative embodiment of a pivot joint unit of a pivot joint assembly, in accordance with the present invention.

Looking next to FIGS. 2 and 2A, presented therein are a perspective view and an exploded perspective view, respectively, of one illustrative embodiment of a pivot joint unit 121 of a pivot joint assembly 120, in accordance with the present invention. As before, a pivot joint unit 121 includes at least two pivot joint members 122 interconnected in a movable relation to one another. As shown in FIGS. 2 and 2A, the pivot joint unit 121 comprises three pivot joint members 122, with the outer pivot joint members 122 positioned in one direction, while the middle pivot joint member 122 is, at least initially, positioned in an opposite direction. A pivot joint member 122 in accordance with at least one embodiment of the present invention comprises a pivot end 123, and an oppositely disposed fixed end 128. A fixed end 128 of a pivot joint member 122 includes a fixed end interconnect 129 to allow a portion of the pivot joint member 122 to be secured in a fixed position, while the pivot end 123 remains at least partially movable relative to a pivot member 126, as is described in detail hereinafter.

A pivot joint member 122 of a pivot joint unit 121 may be constructed of any of a variety of materials provided they exhibit sufficient strength and rigidity based upon the loading characteristics to be encountered by a specific application for a damped pivot joint assembly 110 of a damped articulation system 100 in accordance with the present invention. As such, in one embodiment, wherein a damped pivot joint assembly 110 is to be subjected to considerable loads, each of a plurality of pivot joint members 122 may be constructed of a metal or metal alloy such as aluminum, steel, stainless steel, etc., just to name a few. Alternatively, when a damped pivot joint assembly 110 is only going to be subjected to lighter loads, each of a plurality of pivot joint members 122 may be constructed of one or more of, but is in no manner limited to, a plastic, composite, or engineered material of construction.

In at least one embodiment, a pivot end 123 of a pivot joint member 122 comprises at least one pivot aperture 124 disposed therethrough. With reference once again to FIGS. 2 and 2A, a pivot member 126 is disposed through a pivot aperture 124 formed through the pivot end 123 of each of the plurality of pivot joint members 122 of the pivot joint unit 121. A pivot member 126 in accordance with the present invention is structured and dimensioned such that each of a plurality of pivot joint members 122 are movable thereabout while the pivot member 126 is disposed through a corresponding pivot aperture 124 of the pivot joint members 122.

A bushing 125 may be mounted through at least a portion of a pivot aperture 124 of one or more of a plurality of pivot joint members 122 which comprise a pivot joint unit 121 in accordance with the present invention, in order to facilitate rotational movement of the pivot joint members 122 relative to the pivot member 126 about a pivot axis 127 therethrough. A bushing 125 may be constructed from any of a number of materials exhibiting a low coefficient of friction such as polished stainless steel, brass, bronze, nylon, polytetrafluoroethylene, more commonly known as TEFLON®, polyoxymethylene, or ultrahigh molecular weight polyethylene, just to name a few.

In at least one embodiment, such as is shown best in FIG. 2A, each of the plurality of pivot joint members 122 is rotationally movable relative to pivot member 126 about pivot axis 127 therethrough. As further shown in the illustrative embodiment of FIG. 2A, the pivot member 126 comprises a bolt member having an enlarged head, so as to prevent passage through a pivot aperture 124 of a pivot joint member 122, and is configured to thread onto an oppositely disposed barrel screw, also having an enlarged head, once again, so as to prevent passage through a pivot aperture 124 of a pivot joint member 122. It is to be appreciated that it is within the scope and intent of the present invention for a pivot member 126 to comprise any of a number of physical configurations including but not limited to a pin and cotter key, a split pin, a rivet, etc., provided that corresponding ones of a plurality of pivot joint members 122 are movable relative to the pivot member 126.

To facilitate rotational movement of each of a plurality of pivot joint members 122 about a pivot member 126, in at least one embodiment of the present invention, a pivot joint unit 121 further comprises a bearing assembly 130. More in particular, a bearing assembly 130 includes at least one bearing unit 131 disposed between adjacent ones of the plurality of pivot joint members 122. As may be seen from the illustrative embodiment of FIG. 2, a bearing assembly 130 comprises a plurality of bearing units 131, each disposed between different adjacent ones of the plurality of pivot joint members 122 of the pivot joint unit 121.

Looking with reference to FIG. 2A, a bearing unit 131 of a bearing assembly 130 in accordance with at least one embodiment of the present invention comprises a bearing member 132 having a bearing member aperture 133 disposed through a portion thereof. As shown in FIG. 2A, bearing member 132 comprises a needle roller thrust bearing having a plurality of individual roller thrust bearings disposed therearound and radiating outwardly from the bearing member aperture 133 disposed therethrough. A bearing unit 131 may further comprise a bearing interface 134 which is dimensioned and configured to be positioned in contact with the individual roller thrust bearings of a bearing member 132 on one side and in contact with a portion of a corresponding pivot joint member 122 on an opposite side. In at least one embodiment, a bearing unit 131 comprises a plurality of bearing interfaces 134 each dimensioned and configured to be positioned in contact with the individual roller thrust bearings of a bearing member 132 on opposite sides thereof, as well as to be in contact with portions of adjacent ones of the plurality of pivot joint members 122 of the pivot joint unit 121, such as is shown best in FIG. 2A. A bearing unit 131 further comprises a bearing shield 136 in at least one embodiment, wherein the bearing shield 136 is dimensioned and configured to at least partially surround and enclose at least a bearing member 132 so as to minimize if not prevent dust, dirt, or other debris from contacting the bearing member 132 and interfering with the operation thereof.

As further shown in FIG. 2A, each bearing interface 134 comprises a bearing interface aperture 135 formed therethrough corresponding to bearing member aperture 133 of the corresponding bearing member 132. As such, a pivot member 126 of a pivot joint unit 121 is free to pass through each bearing member 132 and its corresponding bearing interface(s) 134, such that the bearing unit 131 further facilitates rotation of the plurality of pivot joint members 122 of the pivot joint unit 121 about pivot member 126. In at least one further embodiment, a portion of one or more of a plurality of pivot joint members 122 of a pivot joint unit 121 may be constructed of or at least partially coated with a material having a low coefficient of friction including, but in no manner limited to, polished stainless steel, brass, bronze, nylon, polytetrafluoroethylene, polyoxymethylene, or ultrahigh molecular weight polyethylene, just to name a few, once again, so as to facilitate rotation of the plurality of pivot joint members 122 of the pivot joint unit 121 about pivot member 126.

Figure 3:
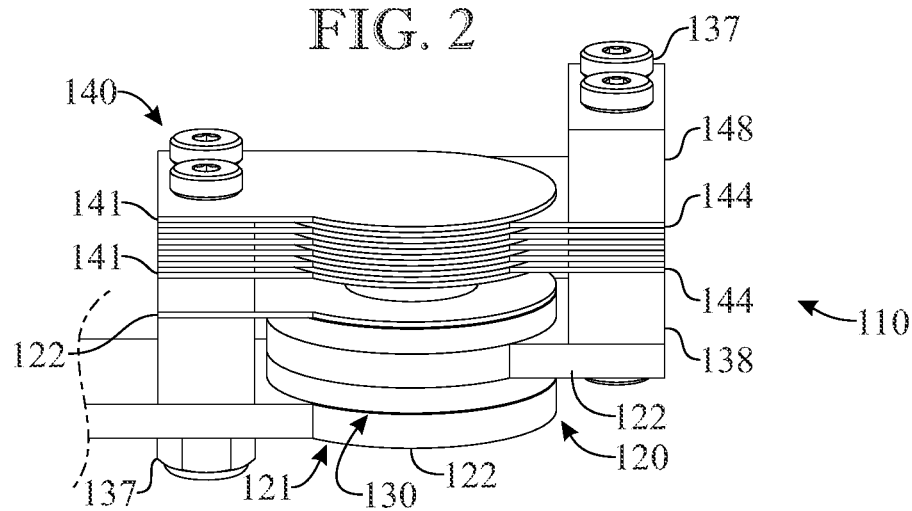
FIG. 3 presents a perspective view of one illustrative embodiment of a damped pivot joint assembly, in accordance with the present invention.
Figure 3A:
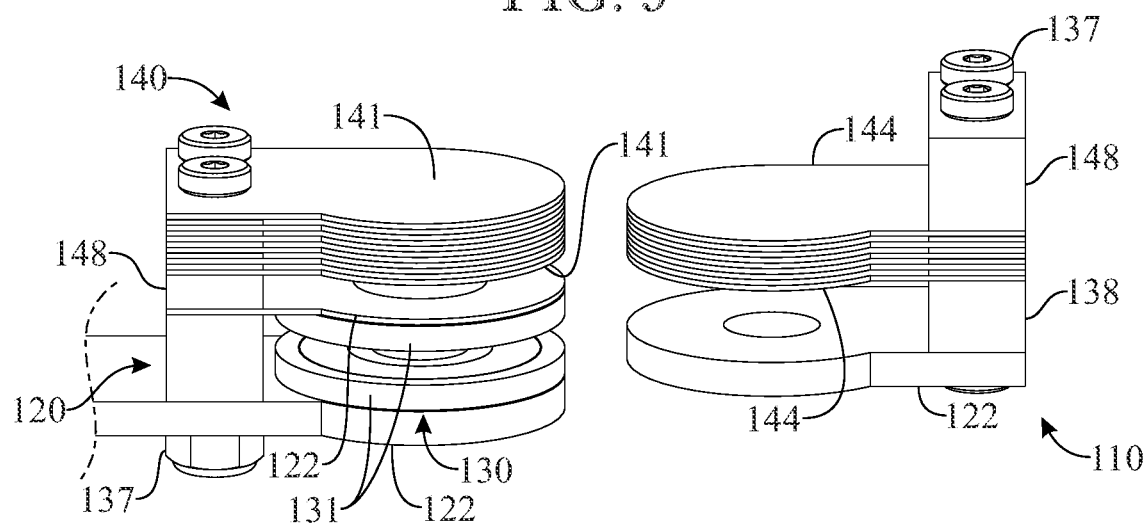
FIG. 3A presents a partially exploded perspective view of the damped pivot joint assembly of FIG. 3, in accordance with the present invention.

Turning next to FIGS. 3 and 3A, presented therein are a perspective view and a partially exploded perspective view, respectively, of one illustrative embodiment of a damped pivot joint assembly 110, in accordance with the present invention. As before, a damped joint assembly 110 in accordance with the present invention comprises a pivot joint assembly 120 having at least one pivot joint unit 121. Also as before, a pivot joint unit 121 comprises a plurality of pivot joint members 122 disposed in an interconnected yet movable relation to one another. In at least one embodiment, a pivot joint unit 121 of a pivot joint assembly 120 may include a bearing assembly 130 having one or more bearing units 131 disposed between adjacent ones of a plurality of pivot joint members 122, once again, so as to facilitate rotation of the plurality of pivot joint members 122 of the pivot joint unit 121 relative to one another such as described hereinabove.

As before, a damped pivot joint assembly 110 further comprises a damping assembly 140. In at least one embodiment, a damping assembly 140 comprises a plurality of primary damping members 141 and a plurality of secondary damping members 144. With reference once again to FIGS. 3 and 3A, each of the plurality of damping members 141, 144 is interconnected to a different one of each of at least two of the pivot joint members 122 of the pivot joint unit 121 and is movable therewith. Further, each of the plurality of primary damping members 141 comprises at least one primary damping surface 142, and each of the plurality of secondary damping members 144 comprises at least one secondary damping surface 145, such as is shown best in the illustrative embodiment of FIG. 4. It is to be appreciated that in at least one embodiment, each of a plurality of damping members 141, 144 comprises at least two oppositely disposed damping surfaces 142, 145. One or more pivot joint spacers 138 and/or damping member spacers 148 may be positioned between one or more pivot joint members 122 and damping members 141, 144 to facilitate operatively positioning each of the plurality of pivot joint members 122 and the plurality of primary and secondary damping members 141, 144 relative to one another in a damped pivot joint assembly 110, such as is shown, by way of example only, in FIG. 4.

Figure 4:
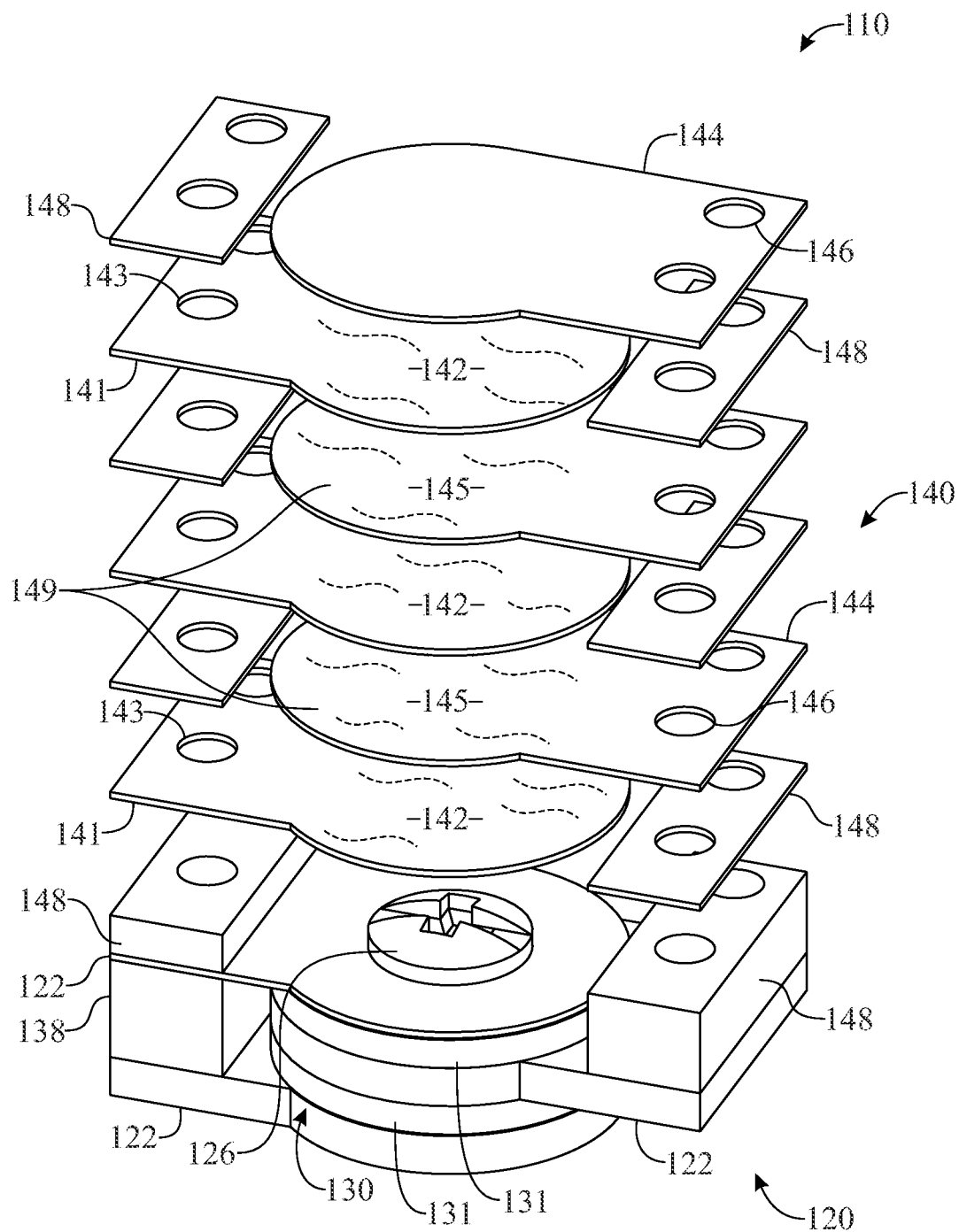
FIG. 4 presents a partially exploded perspective view of another illustrative embodiment of a damped pivot joint assembly, in accordance with the present invention.

As also shown in FIG. 4, a damping member spacer 148, in at least one embodiment, comprises a thickness which is slightly greater than a thickness of a corresponding one of the plurality of oppositely disposed primary damping members 141 or secondary damping members 144, and more in particular, slightly greater than the greatest thickness between oppositely disposed primary damping surfaces 142 or secondary damping surfaces 145, respectively, so as to assure that the corresponding primary damping members 141 and secondary damping members 144 are free to move relative to one another.

One or more fasteners 137 may be utilized to interconnect a plurality of pivot joint members 122 and a plurality of primary and secondary damping members 141, 144, and one or more corresponding ones of a pivot joint spacer 138 and/or a damping member spacer 148 to one another to form a damped pivot joint assembly 110 in accordance with the present invention. As may also be seen from FIGS. 3 and 3A, a fastener 137 comprises nut and bolt combination, however, it is to be appreciated that a fastener 137 may comprise any number of mechanical fasteners including nuts and bolts, as shown in figures, screws, rivets, welds, solder joints, etc., just to name a few. Similarly, as shown in FIGS. 2 through 4, a fixed end interconnect 129 of a pivot joint member 122, a primary damping member interconnect 143, and a secondary damping member interconnect 146 comprise apertures through which a nut and bolt fastener 137, such as is shown in FIG. 1, may pass therethrough. However, it is to be appreciated that in at least one embodiment, one or more of a fixed end interconnect 129, a pivot joint spacer 138, a damping member spacer 148, a pivot joint unit linkage 139, a primary damping member interconnect 143, and/or a secondary damping member interconnect 146 may be drilled and tapped to facilitate interconnection thereto by a threaded bolt, thus eliminating the need for a separate nut.

In accordance with at least one embodiment, a damping surface 142, 145 of each of a plurality of damping members 141, 144 is disposed in an operative contacting orientation with at least one damping surface 145, 142 of a different one of the plurality of damping members 144, 141. More in particular, and with reference once again to FIG. 4, in at least one further embodiment, a primary damping surface 142 of each of a plurality of primary damping members 141 is disposed in an operative contacting orientation with at least one secondary damping surface 145 of a different one of a plurality of secondary damping members 144, and vice versa.

In at least one embodiment, at least one of a primary damping member 141 and/or a secondary damping member 144, and more importantly, at least one of a primary damping surface 142 and/or a secondary damping surface 145 of a plurality of primary and/or secondary damping members 141, 144, are constructed of a material having a low coefficient of friction such as, once again, by way of example only, but in no manner limited to, polished stainless steel, brass, bronze, nylon, polytetrafluoroethylene, polyoxymethylene, or ultrahigh molecular weight polyethylene, just to name a few.

A damping assembly 140 in accordance with at least one embodiment of the present invention further comprises a damping compound 149 disposed between adjacent ones of at least some of a plurality of damping surfaces 142, 145 disposed in an operative contacting orientation with one another. With reference once again to FIG. 4, in at least one embodiment, a damping compound 149 is disposed on each primary and secondary damping surface 142, 145 which are disposed in an operative contacting orientation with one another. A damping compound 149, in at least one embodiment of the present invention, exhibits a dynamic viscosity sufficient to minimize oscillation of a damped pivot joint assembly 110 during movement by a user afflicted with any degree of tremors, and more in particular, to minimize oscillation of the pivot joint members 122, each having at least one of a plurality of damping members 141, 144 interconnected thereto, relative to one another.

A damping compound 149 may comprise any of a number of oils, greases, polymeric materials, etc., such as exhibit the necessary viscosity and shear stability at normal operating room temperatures sufficient to minimize oscillation of the pivot joint members 122. In at least one embodiment, a damping compound 149 exhibits a dynamic viscosity of about 500 to about 20,000 centipoise at normal operating room temperatures. In one further embodiment, a damping compound 149 exhibits a dynamic viscosity of about 1,000 to about 15,000 centipoise at normal operating room temperatures. In yet another embodiment, a damping compound 149 exhibits a dynamic viscosity of about 2,000 to about 12,000 centipoise at normal operating room temperatures, and in still one further embodiment, a damping compound 149 comprises a dynamic viscosity of at least about 2,000 centipoise at normal operating room temperatures. In yet one further embodiment, a damping compound 149 exhibits a dynamic viscosity of about 10,000 to about 12,000 centipoise at normal operating room temperatures, and in still another embodiment, a damping compound 149 comprises a dynamic viscosity of about 11,000 centipoise, once again, at normal operating room temperatures.

In at least one other embodiment, a damping compound 149 comprises a higher dynamic viscosity of about 20,000 to about 100,000 centipoise at normal operating room temperatures. In still one further embodiment, a damping compound 149 comprises a very high dynamic viscosity of about 100,000 to about 300,000 centipoise at normal operating room temperatures. As will be appreciated, in such an embodiment, considerably smaller amounts of a damping compound 149 may be required and/or the physical dimensions of the plurality of damping surfaces 142, 145 may be significantly reduced.

In one further embodiment, a damping compound 149 may be characterized in terms of its NLGI consistency number, also known as an NLGI consistency grade, such as are established by the National Lubricating Grease Institute. More in particular, the higher the NLGI number of grade, the thicker the consistency of the material in question is. In one embodiment, a damping compound 149 in accordance with the present invention comprises an NLGI consistency grade of 0-1 to 4-5. In one further embodiment, a damping compound 149 in accordance with the present invention comprises an NLGI consistency grade of 1-2 to 3-4, and in yet one further embodiment, a damping compound 149 comprises an NLGI consistency grade of 3.

In at least one embodiment, a damping compound 149 comprises a silicone based organo-polymeric material, such as a silicone based oil or silicone based grease. Use of a silicone based grease as a damping compound 149 provides for low friction between each of a plurality of primary damping members 141 disposed in an operative contacting orientation with a plurality of secondary damping members 144, which allows a damped pivot joint assembly 110 of the present damped articulation system 100 to be easily articulated to any of a number of operable positions. Further, while exhibiting desirable low friction qualities, a damping compound 149 comprising a silicone based grease in accordance with at least one embodiment of the present invention further exhibits a very high shear stability. Shear stability is a measure of the resistance of a compound to changes in viscosity, when the compound is subjected to mechanical stress or shear. As a result, when a compound exhibiting high shear stability is disposed between each of a plurality of primary damping members 141 disposed in an operative contacting orientation with a plurality of secondary damping members 144 of a damped pivot joint assembly 110, rapid oscillation of the damped pivot joint assembly 110 during movement thereof is precluded. In accordance with at least one embodiment of the present invention, a damping compound 149 comprises an amount of polydimethylsiloxane.

Figure 5:
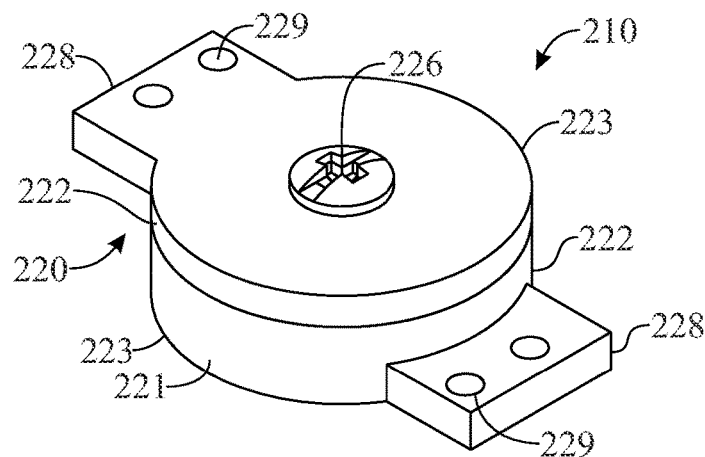
FIG. 5 presents a perspective view of one alternative illustrative embodiment of a damped pivot joint assembly, in accordance with the present invention.
Figure 5A:
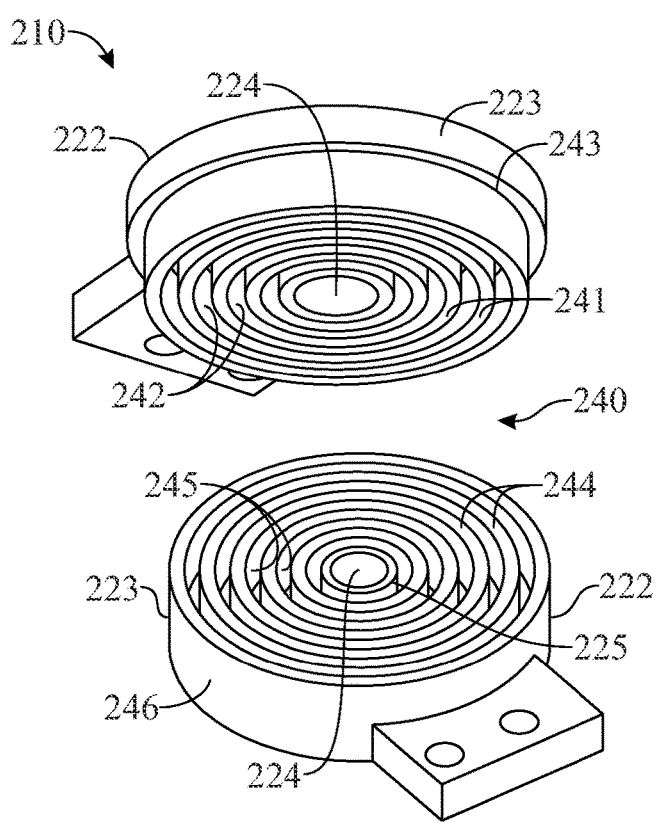
FIG. 5A presents a partially exploded perspective view of the damped pivot joint assembly of FIG. 5, in accordance with the present invention.

Alternative embodiments are contemplated in addition to the embodiments(s) shown and/or described herein. As one example, FIGS. 5 and 5A present perspective and partially exploded perspective views, respectively, of one alternative illustrative embodiment of a damped pivot joint assembly 210, in accordance with the present invention. As before, the damped pivot joint assembly 210 comprises a pivot joint assembly 220 including at least one pivot joint unit 221 comprising a plurality of pivot joint members 222. Also as before, each of the plurality of pivot joint members 222 comprise a pivot end 223 and an oppositely disposed fixed end 228.

With continued reference to the illustrative embodiment of FIGS. 5 and 5A, the pivot end 223 of each pivot joint member 222 comprises a pivot aperture 224 disposed therethrough. Similar to pivot joint unit 121 described and disclosed herein above, pivot joint unit 221 also includes a pivot member 226 operatively positioned through corresponding ones of pivot apertures 224 of each pivot joint member 222 such that each pivot joint member 222 is rotationally movable relative to a pivot member 226 about a pivot axis therethrough. As before, a bushing 225 may be mounted through at least a portion of a pivot aperture 224 of one or more of a plurality of pivot joint members 222 which comprise a pivot joint unit 221 in accordance with the present invention, in order to facilitate rotational movement of each pivot joint member 222 relative to the pivot member 226 about a pivot axis therethrough. Also as before, a bushing 225 may be constructed from any of a number of materials exhibiting a low coefficient of friction such as polished stainless steel, brass, bronze, nylon, polytetrafluoroethylene, polyoxymethylene, or ultrahigh molecular weight polyethylene, etc.

This alternative embodiment of a damped pivot joint assembly 210 further comprises a damping assembly 240. A damping assembly 240 in at least one embodiment includes a plurality of primary damping members 241 and a corresponding plurality of secondary damping members 244. As before, each of a plurality of primary damping members 241 comprise at least one primary damping surface 242, and likewise, each of the plurality of secondary damping members 244 comprise at least one secondary damping surface 245, wherein corresponding ones of a primary damping surface 242 of each of the plurality of primary damping members 241 and a secondary damping surface 245 of an adjacent one of the plurality of secondary damping members 244 are configured and dimensioned to be disposed in an operative contacting orientation with one another.

In at least one embodiment, at least one of a primary damping member 241 and/or a secondary damping member 244, and more importantly, at least one of a primary damping surface 242 and/or a secondary damping surface 245 of a plurality of primary and/or secondary damping members 241, 244, is constructed of a material having a low coefficient of friction such as, once again, by way of example only, but in no manner limited to, polished stainless steel, brass, bronze, nylon, polytetrafluoroethylene, polyoxymethylene, or ultrahigh molecular weight polyethylene, just to name a few.

As may be seen from the illustrative embodiment of FIGS. 5 and 5A, each of the plurality of primary damping members 241 and the primary damping surfaces 242 disposed thereon comprise concentric rings of varied diameters arranged within one another and interconnected to a pivot joint member 222 by a primary damping member interconnect 243. Similarly, each of the plurality of secondary damping members 244 and the secondary damping surfaces 245 disposed thereon also comprise concentric rings of varied diameters arranged within one another and interconnected to a different pivot joint member 222 by a secondary damping member interconnect 246. As will be appreciated from the illustrative embodiments of FIGS. 5 and 5A, when the oppositely disposed pivot joint members 222 rotate relative to one another about pivot member 226, adjacent ones of the primary and secondary damping surfaces 242, 245 of the primary and secondary damping members 241, 244 will also rotate with the corresponding one of the plurality of pivot joint member 222 to which they are interconnected, while remaining disposed in a contacting orientation with one another.

As before, a damping compound 149, such as is described hereinabove, may be disposed on or between adjacent ones of the primary and secondary damping surfaces 242, 245 of the primary and secondary damping members 241, 244, once again, to minimize oscillation of a damped pivot joint assembly 210 during movement by a user afflicted with any degree of tremors, and more in particular, to minimize oscillation of the pivot joint members 222, each having at least one of a plurality of damping members 241, 244 interconnected thereto, relative to one another.

Figure 6:
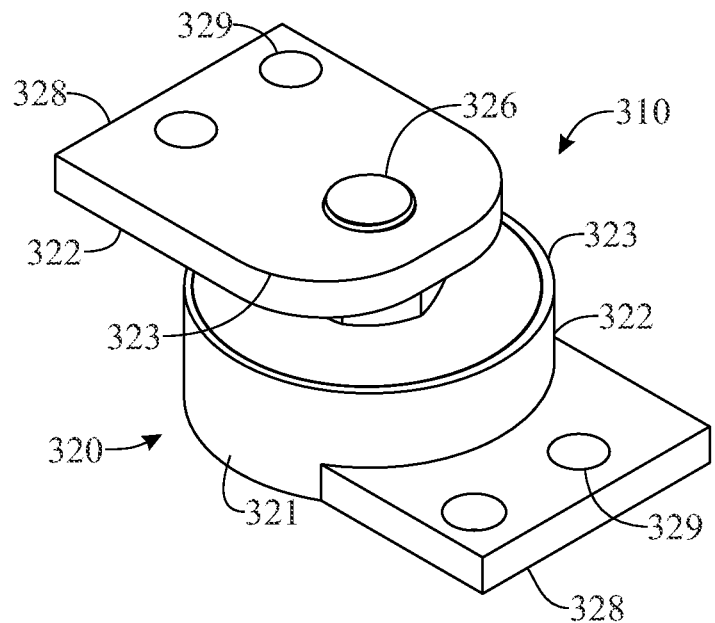
FIG. 6 presents a perspective view of another alternative illustrative embodiment of a damped pivot joint assembly, in accordance with the present invention.
Figure 6A:
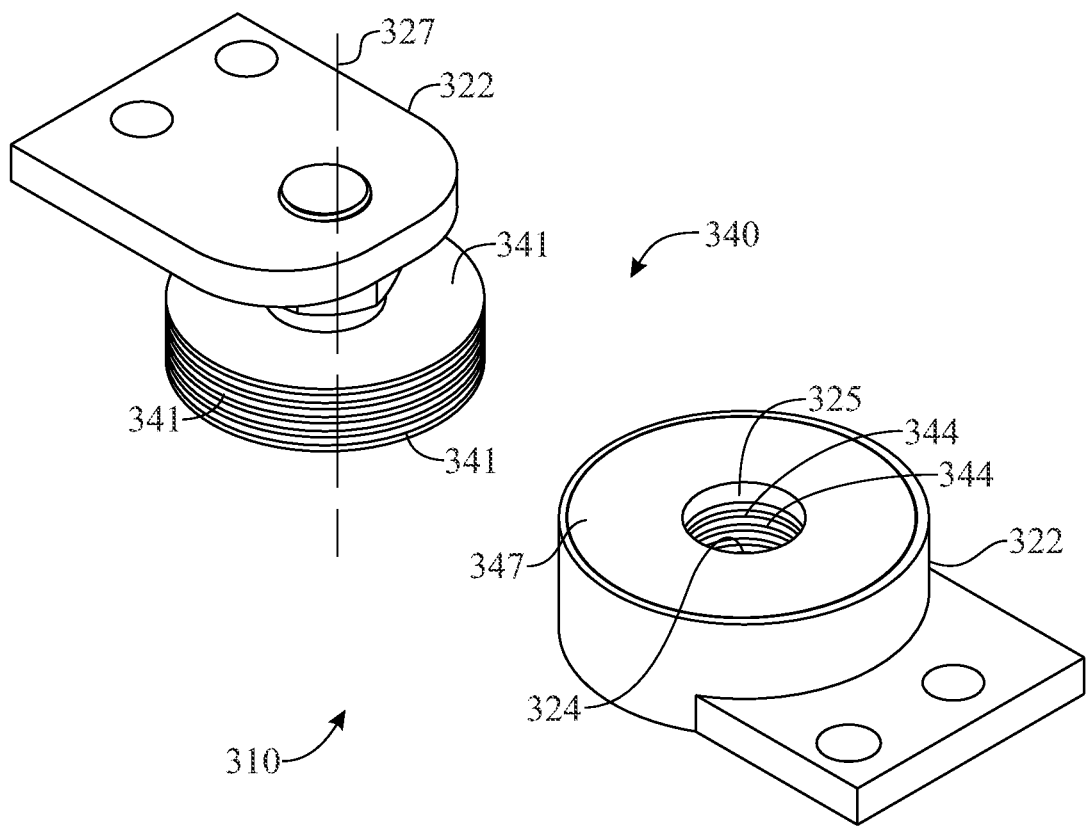
FIG. 6A presents a partially exploded perspective view of the damped pivot joint assembly of FIG. 6, in accordance with the present invention.

Looking next to FIGS. 6 and 6A, presented therein are a perspective view and a partially exploded perspective view, respectively, of another alternative illustrative embodiment of a damped pivot joint assembly 310, in accordance with the present invention. Once again, a damped pivot joint assembly 310 comprises a pivot joint assembly 320 including at least one pivot joint unit 321 comprising a plurality of pivot joint members 322. As before, each of the plurality of pivot joint members 322 comprise a pivot end 323 and an oppositely disposed fixed end 328.

In one embodiment, a pivot end 323 of each pivot joint member 322 comprises a pivot aperture 324 disposed therethrough. Similar to pivot joint unit 121 described and disclosed herein above, pivot joint unit 321 also includes a pivot member 326 operatively positioned through corresponding ones of pivot apertures 324 of each pivot joint member 322 such that each pivot joint member 322 is rotationally movable relative to a pivot member 326 about a pivot axis 327 therethrough. A bushing 325 may be mounted through at least a portion of a pivot aperture 324 of one or more of a plurality of pivot joint members 322 which comprise the alternative embodiment of the pivot joint unit 321 in accordance with the present invention. As before, bushing 325 facilitates rotational movement of each pivot joint member 322 relative to a pivot member 326 about a pivot axis 327 therethrough. Also as before, a bushing 325 may be constructed from any of a number of materials exhibiting a low coefficient of friction such as polished stainless steel, brass, bronze, nylon, polytetrafluoroethylene, polyoxymethylene, or ultrahigh molecular weight polyethylene, just to name a few.

The alternative embodiment of a damped pivot joint assembly 310 further comprises a damping assembly 340. A damping assembly 340 in at least one embodiment includes a plurality of primary damping members 341 and a corresponding plurality of secondary damping members 344. As before, each of a plurality of primary damping members 341 comprise at least one primary damping surface 342, and likewise, each of the plurality of secondary damping members 344 comprise at least one secondary damping surface 345, such as is shown best in the illustrative embodiment of FIG. 7. In at least one embodiment, corresponding ones of a primary damping surface 342 of each of the plurality of primary damping members 341 and a secondary damping surface 345 of an adjacent one of the plurality of secondary damping members 344 are configured and dimensioned to be disposed in a contacting orientation with one another.

In at least one embodiment, at least one of a primary damping member 341 and/or a secondary damping member 344, and more importantly, at least one of a primary damping surface 342 and/or a secondary damping surface 345 of a plurality of primary and/or secondary damping members 341, 344, are constructed of a material having a low coefficient of friction such as, once again, by way of example only, but in no manner limited to, polished stainless steel, brass, bronze, nylon, polytetrafluoroethylene, polyoxymethylene, or ultrahigh molecular weight polyethylene, just to name a few.

Figure 7:
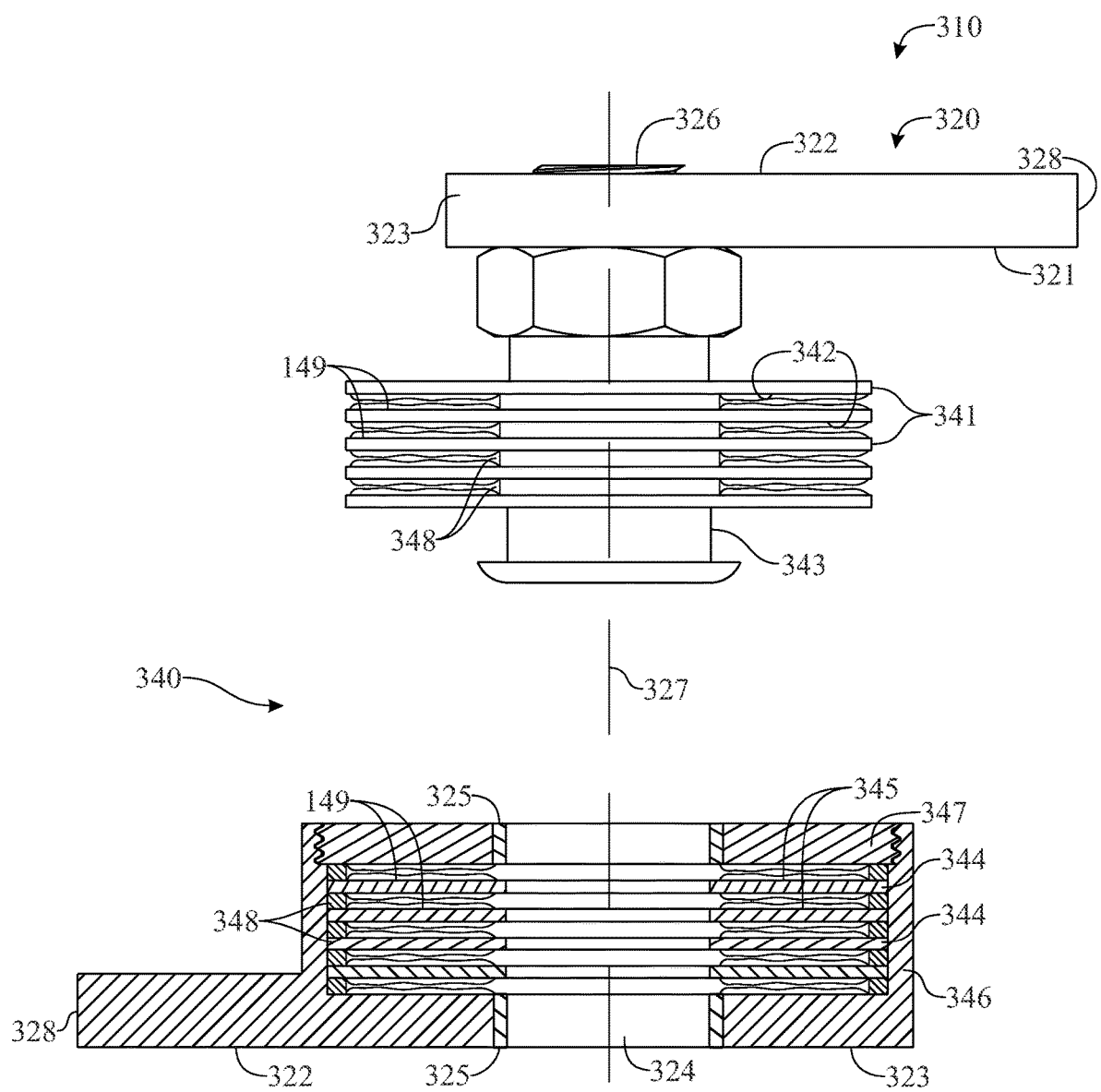
FIG. 7 presents a partially exploded partial cross-sectional view of the damped pivot joint assembly of FIG. 6, in accordance with the present invention.

As may be seen best from the illustrative embodiment of FIG. 7, each of the plurality of primary damping members 341 comprises a generally washer-like configuration arranged in a slightly spaced apart relation to one another and interconnected to one pivot joint member 322 by a primary damping member interconnect 343. As before, each of the primary damping members 341 includes a primary damping surface 342 disposed on opposite sides thereof. In at least one embodiment, a primary damping member interconnect 343 may be integral with a pivot member 326, such as is shown in FIG. 7, or it may comprise a separate structure altogether. As also shown in FIG. 7, each of the plurality of secondary damping members 344 also comprises a generally washer-like configuration in a slightly spaced apart relation to one another and interconnected to a different pivot joint member 322 by a secondary damping member interconnect 346. Also as before, each of the secondary damping members 344 includes a secondary damping surface 345 disposed on opposite sides thereof.

In at least one embodiment, a damped pivot joint assembly 310 comprises at least one damping member spacer 348 disposed between adjacent facing ones of the plurality of primary damping members 341 or the plurality of secondary damping members 344. More in particular, in one embodiment, a damping member spacer 348 is disposed in direct contact with adjacent facing ones of the primary damping surfaces 342 of the plurality of primary damping members 341, so as to retain corresponding ones of the primary damping members 341 in a fixed relation relative to a primary damping member interconnect 343. As such, the primary damping members 341, and thus, the corresponding primary damping surfaces 342, are rotatable with a corresponding one of the pivot joint member 322 to which they are interconnected. In one further embodiment, a plurality of damping member spacers 348 are disposed in direct contact with adjacent facing ones of the secondary damping surfaces 345, such as is shown by way of example in FIG. 7, so as to retain corresponding ones of the secondary damping members 344 in a fixed relation relative to the secondary damping member interconnect 346. Once again, the secondary damping members 344, and thus, the corresponding secondary damping surfaces 345, are rotatable with the corresponding pivot joint member 322 to which they are interconnected. As further shown in FIG. 7, a damping member lock 347 is provide in at least one embodiment so as to compress the plurality of damping member spacers 348 between corresponding ones of the secondary damping members 344.

In at least one other embodiment, a plurality of damping member spacers 348 are disposed in direct contact with adjacent facing ones of a plurality of primary damping surfaces 342, so as to retain corresponding ones of the primary damping members 341 in a fixed relation relative to the primary damping member interconnect 343 such that the primary damping members 341, and thus, the corresponding primary damping surfaces 342, are rotatable with the corresponding pivot joint member 322 to which they are interconnected. In at least one further embodiment, a damping member spacer 348 comprises a material of construction exhibiting a high coefficient of friction relative to the corresponding primary or secondary damping surfaces 342, 345.

As before, a damping member spacer 348, in at least one embodiment, comprises a thickness which is slightly greater than a thickness of a corresponding one of the plurality of oppositely disposed primary damping members 341 or secondary damping members 344, and more in particular, slightly greater than the greatest thickness between oppositely disposed primary damping surfaces 342 or secondary damping surfaces 345, respectively, so as to assure that the corresponding primary damping members 341 and secondary damping members 344 are free to move relative to one another.

It is to be appreciated that, in at least one embodiment, at least one of a plurality of primary damping members 341 and/or a plurality of secondary damping members 344 may be keyed to correspond to a complimentary key disposed on a portion of a primary damping member interconnect 343 and/or a secondary damping member interconnect 346, respectively, once again, so as to retain corresponding ones of the primary and/or secondary damping members 341, 344 in a fixed relation relative to the primary or secondary damping member interconnect 343, 346, such that the primary or secondary damping members 341, 344, and thus, the corresponding primary or secondary damping surfaces 342, 345, are rotatable with the corresponding pivot joint member 322 to which they are interconnected.

Alternatively, one or more of a plurality of primary damping members 341 or of a plurality of secondary damping members 344 may be keyed to correspond to a complimentary key disposed on a portion of a pivot member 326, once again, so as to retain corresponding ones of the primary or secondary damping members 341, 344 in a fixed relation relative to the pivot member 326, such that the primary or secondary damping members 341, 344, and thus, the corresponding primary or secondary damping surfaces 342, 344, are rotatable with the corresponding pivot joint member 322 to which they are interconnected.

As will be appreciated from the illustrative embodiments of FIGS. 6, 6A and 7, when pivot joint members 322 rotate relative to one another about pivot member 326, adjacent ones of the primary and secondary damping surfaces 342, 345 of the primary and secondary damping members 341, 344 will also rotate with the corresponding pivot joint member 322 to which they are interconnected, while remaining disposed in an operative contacting orientation with one another. As before, a damping compound 149, such as is described hereinabove, may be disposed on and/or between adjacent ones of the primary and secondary damping surfaces 342, 345 of the primary and secondary damping members 341, 344, once again, to minimize oscillation of a damped pivot joint assembly 310 during movement by a user afflicted with any degree of tremors, and more in particular, to minimize oscillation of the pivot joint members 322, each having at least one of a plurality of damping members 341, 344 interconnected thereto, relative to one another.

Figure 8:
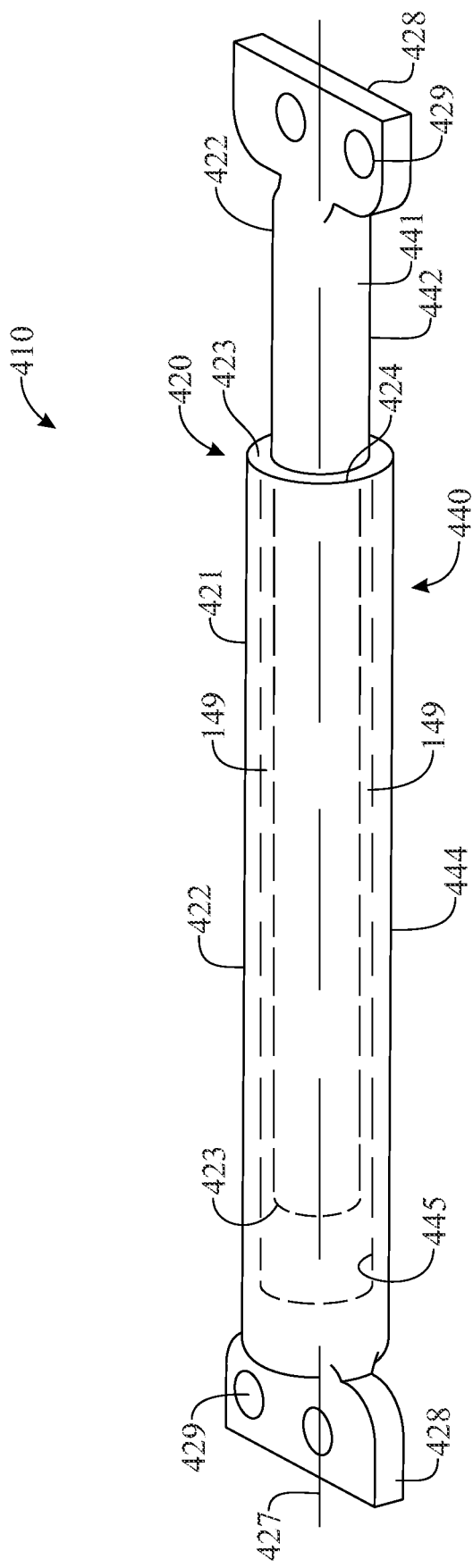
FIG. 8 presents a perspective view of one further alternative illustrative embodiment of a damped pivot joint assembly, in accordance with the present invention.

Looking next to FIG. 8, presented therein is one further alternative illustrative embodiment of a damped pivot joint assembly 410, in accordance with the present invention. As in each of the previously disclosed embodiments, a damped pivot joint assembly 410 comprises a pivot joint assembly 420 having a pivot joint unit 421 comprising a plurality of pivot joint members 422. As before, each of the plurality of pivot joint members 422 comprise a pivot end 423 and an oppositely disposed fixed end 428. Also as before, each fixed end 428 comprises a fixed end interconnect 429 to facilitate interconnection of the damped pivot joint assembly 410 to a damped articulation system 100 in accordance with the present invention, such as via one or more fasteners 137 as described and disclosed hereinabove.

Also as before, a damped pivot joint assembly 410 comprises a damping assembly 440. In accordance with at least one embodiment, a damping assembly 440 includes a primary damping member 441. As may be seen from FIG. 8, a primary damping member 441 comprises a cylindrical configuration having a primary damping surface 442 disposed therearound. As further shown in the illustrative embodiment of FIG. 8, a secondary damping member 444 comprises a complimentary cylindrical configuration comprising a cylindrical channel therethrough at least partially defining a secondary damping surface 445 disposed therearound. As before, the primary damping surface 442 of the primary damping member 441 and the secondary damping surface 445 of the secondary damping member 444 are configured and dimensioned to be disposed in an operative contacting orientation with one another, such as is shown best in FIG. 8.

In at least one embodiment, a primary damping member 441 and/or a secondary damping member 444, and more importantly, a primary damping surface 442 and/or a secondary damping surface 445, are constructed of a material having a low coefficient of friction such as, once again, by way of example only, polished stainless steel, brass, bronze, nylon, polytetrafluoroethylene, polyoxymethylene, or ultra-high molecular weight polyethylene, just to name a few.

A damping compound 149, such as is described hereinabove, may be disposed on one or both of the primary damping surface 442 and the secondary damping surfaces 445 of the primary damping member 441 and the secondary damping member 444, respectively, once again, to minimize oscillation of a damped pivot joint assembly 410 during movement by a user afflicted with any degree of tremors, and more in particular, to minimize oscillation of the pivot joint members 422, each having at least one damping member 441, 444 interconnected thereto in an operative contacting relation to one another.

It is to be appreciated that, given its unique configuration in accordance with at least one embodiment of the present invention, a damped pivot joint assembly 410 may also function as an articulating arm assembly 150, as described hereinabove.

Figure 9:
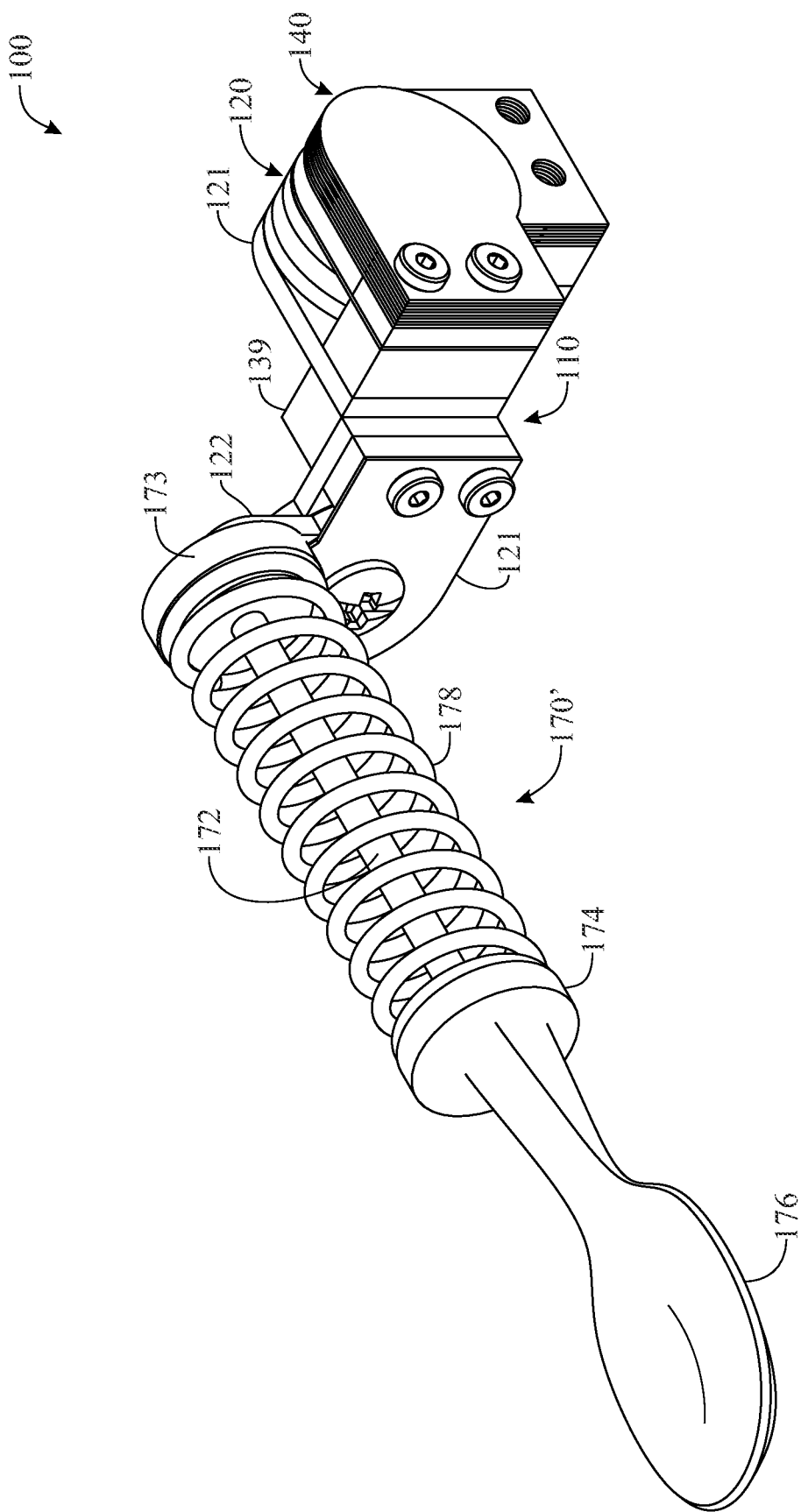
FIG. 9 presents a perspective view of a portion of one illustrative embodiment of a damped articulation system including a biased handle damper member, in accordance with the present invention.

Turning next to FIG. 9, presented therein is a perspective view of a portion of one illustrative embodiment of a damped articulation system 100 including a biased handheld implement assembly 170', in accordance with the present invention. As may be seen from FIG. 9, the damped articulation system 100 comprises a damped pivot joint assembly 110 including a pivot joint assembly 120 comprising a plurality of pivot joint units 121, and a damping assembly 140 operatively interconnected to one of the plurality of pivot joint units 121, as described hereinabove.

A pivot joint unit linkage 139 is provided to facilitate the interconnection of each of the adjacent pivot joint units 121 to one another. A pivot joint unit linkage 139 may be attached to each of a plurality of pivot joint units 121 by any of a number of mechanical fastening mechanisms including bolts, screws, rivets, welds, solder joints, adhesives, etc., thereby interconnecting the plurality of pivot joint units 121 to one another.

As further shown in FIG. 9, the damped articulation system 100 comprises a biased handheld implement assembly 170' including an implement handle 172 having a handle interconnect 173 along one end thereof to facilitate interconnection of the biased handheld implement assembly 170' to a terminal pivot joint unit 121. An implement handle 172 in at least one further embodiment also includes an implement interconnect 174 to facilitate interconnection of at least one handheld implement 176 thereto in an operative orientation. As used herein, an operative orientation of a handheld implement 176 is at least partially defined by a handheld implement 176 being interconnected to a portion of a damped pivot joint assembly 110 in a manner that permits a user to grasp an implement handle 172 and move the handheld implement 176 along and around a working area on a support surface SS.

In at least one further embodiment, and as shown in FIG. 9, a biased handheld implement assembly 170' further comprises a biased handle damper member 178. A biased handle damper member 178 acts to provide an initial damping effect to the handheld implement 176 when the biased handle damper member 178 is grasped by a user during movement of a handheld implement 176 by the user, regardless of whether or not the user is afflicted with any degree of tremors in his or her hand.

Figure 10:
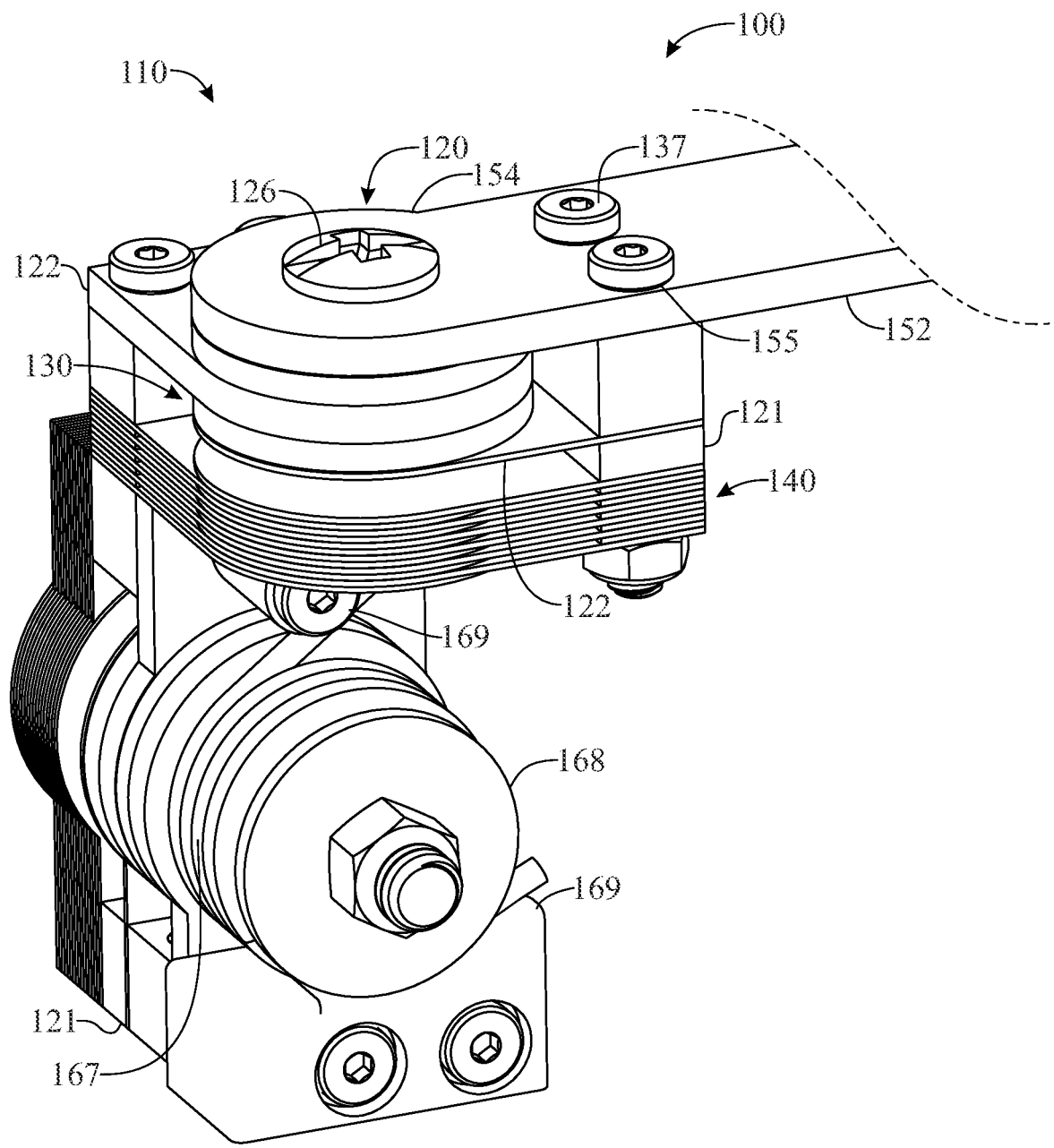
FIG. 10 presents a perspective view of a portion of the damped articulation system of FIG. 1, in accordance with the present invention.

At the opposite end of at least one embodiment of a damped articulation system 100 in accordance with the present invention is a biased support member 167 which serves to provide an initial damping effect at a proximal end of a damped pivot joint assembly 110. As may be seen in FIG. 10, in at least one embodiment, a damped articulation system 100 includes a biased member mount 168 interconnected to a proximal end of a damped pivot joint assembly 110 and dimensioned and configured to retain a biased support member 167 therein. As shown in FIG. 10, in at least one embodiment, the biased support member 167 comprises a heavy gauge coiled spring having opposite ends abutting oppositely disposed biasing member stops 169, thereby maintaining the biased support member 167 in a constant state of compression, and thereby providing a resistive force against movement of the terminal pivot joint unit 121 and damping the effect of movement thereof. In at least one embodiment, a biased support member 167 positioned in a biased member mount 168 serves to at least partially support the weight of a damped articulation system 100 disposed in an operative orientation, in accordance with the present invention. In at least one further embodiment, a biased support member 167 is provided proximate at least one damped pivot joint assembly 110, 210, 310 or 410 in accordance with the present damped articulation system 100 so as to return the damped pivot joint assembly 110, 210, 310 or 410 to an initial position upon movement therefrom and subsequent release by a user.

Figures 11, 11A:
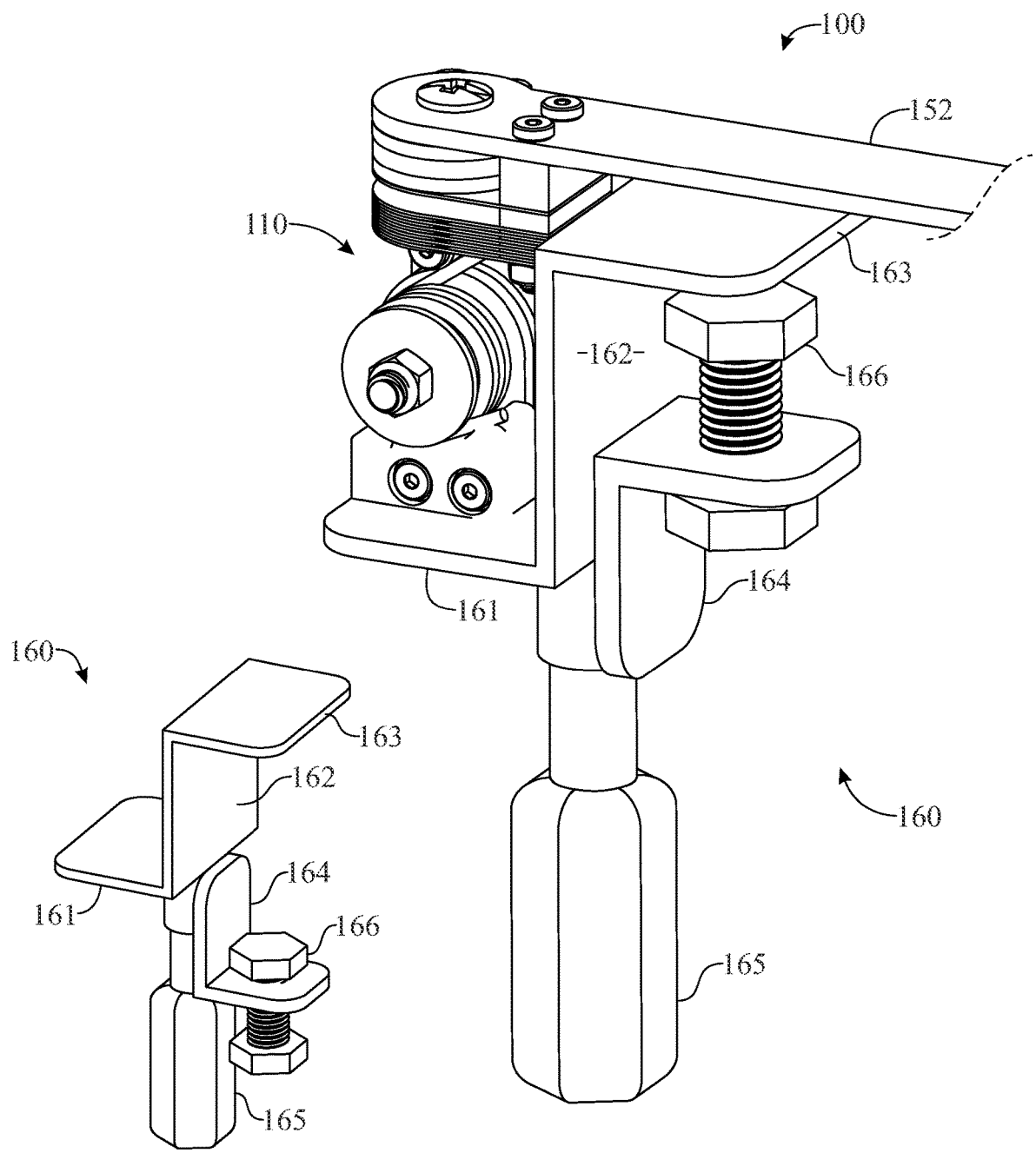
FIG. 11 presents an alternate perspective view of a mounting assembly of the damped articulation system of FIG. 1, in accordance with the present invention.
FIG. 11A presents a perspective view of the mounting assembly of FIG. 11 disposed in an alternate configuration, in accordance with the present invention.

Turning next to FIGS. 11 and 11A, perspective views of a mounting assembly 160 disposed in alternate configurations in accordance with one embodiment of a damped articulation system 100 are presented. As may be seen from FIG. 11, a mounting assembly 160 in one embodiment includes a base 161 and a fixed mount member 163 interconnected to one another via a sidewall 162. A proximal end of a damped pivot joint assembly 110 is mounted to a base 161 of a mounting assembly 160, in accordance with at least one embodiment of the present damped articulation system 100.

A mounting assembly 160 in accordance with at least one embodiment of the present invention includes a primary mount adjustment 165 and a secondary mount adjustment 166. With reference once again to FIGS. 11 and 11A, a movable mount member 164 is disposable between a first, upward facing configuration, such as is shown in FIG. 11, to facilitate mounting the present damped articulation system 100 to a support surface SS having a thinner or narrower profile, and a downward facing configuration, such as is shown in FIG. 11A, to facilitate mounting the present damped articulation system 100 to a support surface SS having a thicker or wider profile. Regardless of whether the movable mount member 164 is disposed in an upward or downward facing configuration, primary mount adjustment 165 and secondary mount adjustment 166 are provided such that the present damped articulation system 100 may be secured to a portion of a support surface SS, such as a table or a work bench, by tightening the primary mount adjustment 165 and secondary mount adjustment 166, as needed, until the support surface SS is secured between the fixed mount member 163 and the secondary mount adjustment 166.

Figure 12:
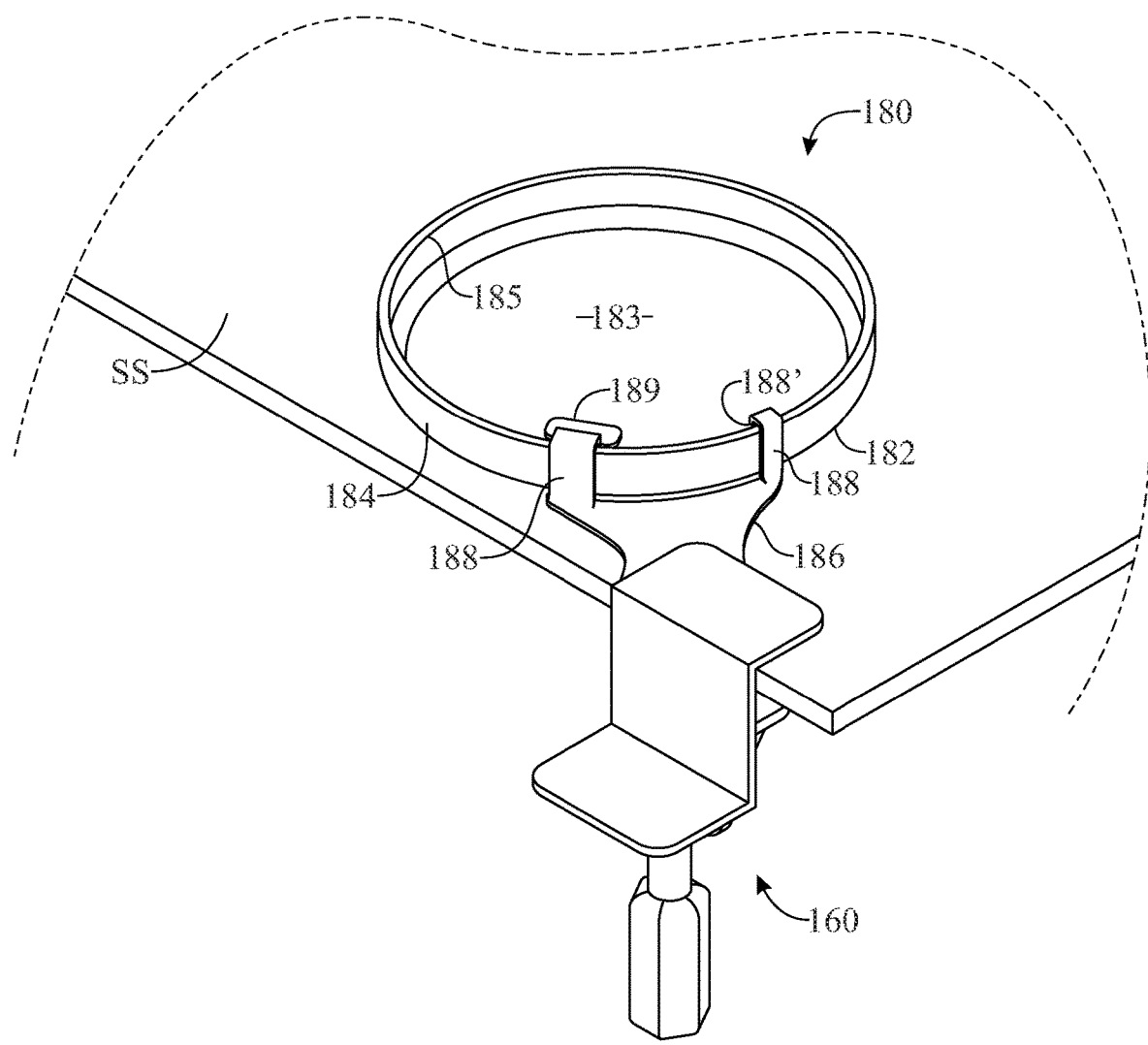
FIG. 12 presents a perspective view of one illustrative embodiment of a serving assembly, in accordance with the present invention.

FIG. 12 provides a perspective view of one illustrative embodiment of a serving assembly 180, in accordance with the present invention. In one embodiment, a serving assembly 180 includes a serving dish 182 having a bottom surface 183 and a sidewall 184 extending upwardly around at least a portion of the bottom surface 183. As shown in FIG. 12, a sidewall 184 extends completely around the bottom surface 183 of the serving dish 182 in a surrounding relation thereto. As further shown in FIG. 12, the sidewall 184 comprises an upper beveled end 185 which serves to facilitate transfer of an amount of food from the serving dish 182 onto a handheld implement 176, in accordance with at least one embodiment of the present invention. In at least one further embodiment, a sidewall 184 is angled inwardly around the bottom surface 183 of the serving dish 182 so as to further facilitate the transfer of an amount of food from the serving dish 182 onto a handheld implement 176.

A mounting assembly 160 is provided to secure a serving dish 182 onto a portion of a support surface SS during use. As will be appreciated, in at least one embodiment, the same mounting assembly 160 may be utilized to attach a damped pivot joint assembly 110 to a portion of a support surface SS as well, such as described hereinabove. Alternatively, one mounting assembly 160 may be utilized to attach a damped pivot joint assembly 110 to a support surface SS while another separate mounting assembly 160 is utilized to secure a serving assembly 180 onto a portion of support surface SS during use.

A serving assembly 180 in at least one embodiment further comprises a hold-down bracket 186 attached to at least a portion of a mounting assembly 160. A hold-down bracket 186 includes at least one bracket arm 188 dimensioned and configured to overlie at least a portion of a sidewall 184 of a serving dish 182, so as to at least partially retain the serving dish 182 in position while in use by a person eating therefrom utilizing a handheld implement 176, such as a spoon or a fork, in accordance with the present invention. In at least one embodiment, a hold-down bracket 186 comprises a plurality of bracket arms 188, each dimensioned and configured to overlie a portion of a sidewall 184 of a serving dish 182 to at least partially retain the serving dish 182 in position while in use.

A bracket arm 188 in at least one embodiment comprises a bracket channel 188' dimensioned to allow a portion of a sidewall 184 of a serving dish 182 to be movable therethrough, while maintaining the serving dish 182 on the support surface SS while in use. A scraper 189 may be provided on at least one bracket arm 188, once again, to facilitate transfer of an amount of food from a serving dish 182 onto a handheld implement 176, once again, such as a spoon or a fork, while a user is feeding himself or herself therewith.

As will be appreciated from the foregoing, the present damped articulation system 100 is amenable for use in any number of applications and for operation by users having any degree of hand tremors from mild to severe, or even none at all. More in particular, a damped pivot joint assembly 110, 210, 310, 410 comprising a corresponding damping assembly 140, 240, 340, 440 in accordance with the present invention may be configured for use in any number of applications and/or for operation by users exhibiting any degree of hand tremors from mild to severe, or, once again, none at all.

Specifically, and as is to be appreciated from the foregoing, a damping assembly 140, 240, 340, 440 in accordance with the present invention may include more or fewer damping members 141, 241, 341, 441, 144, 244, 344, 444 in order to increase or decrease a degree of damping resultant therefrom. Additionally or alternatively, a size and/or geometry of one or more damping members 141, 241, 341, 441, 144, 244, 344, 444 may be varied in order to increase or decrease a degree of damping resultant therefrom. Likewise, greater or lesser amounts of a damping compound 149 may be applied to the various damping members 141, 241, 341, 441, 144, 244, 344, 444, once again, resulting in an increase or decrease in a degree of damping provided by a damping assembly 140, 240, 340, 440 in accordance with the present invention. Similarly, a damping compound 149 having a greater or lesser viscosity and/or NLGI grade may be employed thereby providing for a wide range in a degree of damping provided by a damping assembly 140, 240, 340, 440 in accordance with the present invention.

Once again, and as will be truly appreciated from the foregoing, the present damped articulation system 100, and more in particular, a damped pivot joint assembly 110, 210, 310, 410 in accordance with the present invention, is amenable for use in any number of applications and for operation by users having any degree of hand tremors from severe to mild, to none at all.

Since many modifications, variations, and changes in detail can be made to the described embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A damped articulation system to facilitate operation of a handheld implement proximate a support surface by a user afflicted with tremors, said system comprising:
    a damped pivot joint assembly interconnected to a portion of the support surface;
    said damped pivot joint assembly comprising a pivot joint assembly including at least one pivot joint unit having at least two pivot joint members interconnected in a movable relation to one another;
    said damped pivot joint assembly further comprising a damping assembly having a plurality of damping members, at least one of said plurality of damping members interconnected to a different one of each of said at least two pivot joint members and movable therewith;
    each of said plurality of damping members comprising at least one damping surface, said at least one damping surface of each of said plurality of damping members disposed in a contacting orientation with said at least one damping surface of a different one of said plurality of damping members;
    said damping assembly further comprising a damping compound disposed between adjacent ones of said plurality of damping surfaces disposed in said contacting orientation with one another, said damping compound exhibiting a dynamic viscosity sufficient to minimize oscillation of said damped pivot joint assembly during movement of said at least two pivot joint members, each having at least one of said plurality of damping members interconnected thereto, relative to one another; and
    a handheld implement assembly including a handle having said handheld implement attached thereto, said handle further interconnected to a portion of said damped pivot joint assembly.

2. The damped articulation system as recited in claim 1, wherein each of said plurality of pivot members comprises a fixed end and an oppositely disposed pivot end.

3. The damped articulation system as recited in claim 2, wherein each of said plurality of pivot members comprises a pivot aperture through a pivot end thereof.

4. The damped articulation system as recited in claim 3, wherein said at least one pivot joint unit comprises a pivot member operatively positioned through said pivot aperture of each of said plurality of pivot members thereby interconnecting said plurality of pivot members to one another in a movable relation.

5. The damped articulation system as recited in claim 2, wherein said fixed end of at least one of said plurality of pivot members is interconnected to the portion of the support surface.

6. The damped articulation system as recited in claim 2, wherein said fixed end of at least one of said plurality of pivot members is attached to a portion of said handheld implement assembly.

7. The damped articulation system as recited in claim 1, wherein said damping assembly comprises a plurality of damping members interconnected to each of said at least two pivot joint members and movable therewith.

8. The damped articulation system as recited in claim 1, wherein at least some of said plurality of damping members comprise a plurality of damping surfaces.

9. The damped articulation system as recited in claim 8, wherein said plurality of damping surfaces are disposed on opposite sides of a corresponding one of said plurality of damping members.

10. The damped articulation system as recited in claim 9, wherein said plurality of damping surfaces are planar.

11. The damped articulation system as recited in claim 9, wherein said plurality of damping surfaces are concentric.

12. The damped articulation system as recited in claim 9, wherein said plurality of damping members are disposed such that said plurality of damping surfaces are disposed in an alternating contacting relation with one another.

13. The damped articulation system as recited in claim 1, wherein at least some of said plurality of damping surfaces are constructed of a material having a static friction coefficient of about 0.04 to about 0.75.

14. The damped articulation system as recited in claim 1, wherein at least some of said plurality of damping surfaces are constructed of a material having a kinetic friction coefficient of about 0.04 to about 1.25.

15. The damped articulation system as recited in claim 1, wherein at least some of said plurality of damping surfaces are constructed of polished stainless steel.

16. The damped articulation system as recited in claim 1, wherein said damping compound comprises an amount of polydimethylsiloxane.

17. The damped articulation system as recited in claim 1, wherein said damping compound comprises a dynamic viscosity of at least about 2,000 centipoise.

18. The damped articulation system as recited in claim 1, wherein said handheld implement is selected from the group consisting of an eating utensil, a writing instrument, and a handheld tool.

19. A damped articulation system to facilitate operation of a handheld implement proximate a support surface by a user afflicted with tremors, said system comprising:

a mounting assembly dimensioned and configured to be at least temporarily secured to a portion of the support surface;

a damped pivot joint assembly comprising a pivot joint assembly including a plurality of pivot joint units operatively interconnected to one another, wherein at least one of said plurality of pivot joint units is movable in an x-plane, at least one of said plurality of pivot joint units is movable in a y-plane, and at least one of said plurality of pivot joint units is movable in a z-plane;

each of said plurality of pivot joint units having at least two pivot joint members interconnected in a movable relation to one another;

said damped pivot joint assembly further comprising a damping assembly having a plurality of damping members, wherein each of said at least two pivot joint members of at least some of said plurality of pivot joint units comprises a plurality of different ones of said plurality of damping members interconnected thereto and movable therewith;

each of said plurality of damping members comprising at least one damping surface, each said damping surface of each said different ones of said plurality of damping members interconnected to corresponding ones of said at least two pivot joint members of each of said plurality of pivot joint units disposed in an alternating contacting orientation relative to one another;

said damping assembly further comprising a damping compound disposed between adjacent ones of said plurality of damping surfaces, said damping compound exhibiting a dynamic viscosity sufficient to minimize oscillation of said damped pivot joint assembly during movement of said at least two pivot joint members, each having a plurality of damping members interconnected thereto, relative to one another;

an articulating arm assembly having at least one arm member, wherein opposite ends of said at least one arm member are interconnected to different ones of said plurality of pivot joint units;

a handheld implement assembly including a handle having said handheld implement attached thereto, a portion of said handheld implement assembly interconnected to a terminal one of said plurality of pivot joint units; and a proximal one of said plurality of pivot joint units interconnected to a portion of said mounting assembly.

* * * * *